(12) United States Patent
Le

(10) Patent No.: US 11,141,077 B2
(45) Date of Patent: Oct. 12, 2021

(54) DEVICE FOR IMMOBILIZING A SUBJECT IN A MEDICAL SYSTEM

(71) Applicant: SHANGHAI UNITED IMAGING HEALTHCARE CO., LTD., Shanghai (CN)

(72) Inventor: Jiaqian Le, Shanghai (CN)

(73) Assignee: SHANGHAI UNITED IMAGING HEALTHCARE CO., LTD., Shanghai (CN)

( * ) Notice: Subject to any disclaimer, the term of this patent is extended or adjusted under 35 U.S.C. 154(b) by 339 days.

(21) Appl. No.: 15/691,992

(22) Filed: Aug. 31, 2017

(65) Prior Publication Data

US 2019/0059783 A1 Feb. 28, 2019

(30) Foreign Application Priority Data

Aug. 29, 2017 (CN) .......................... 201710758535.9

(51) Int. Cl.
*A61B 5/055* (2006.01)
*A61F 5/37* (2006.01)
*A61N 5/10* (2006.01)

(52) U.S. Cl.
CPC ................ *A61B 5/055* (2013.01); *A61F 5/37* (2013.01); *A61N 5/1077* (2013.01); *A61N 2005/1097* (2013.01)

(58) Field of Classification Search
CPC ..... A47C 27/10; A47C 27/081; A47C 27/082; A47C 27/083; A47C 27/084; A47C 27/086; A61N 2005/1097
See application file for complete search history.

(56) References Cited

U.S. PATENT DOCUMENTS 4,442,834 A * 4/1984 Tucker ................ A61F 5/05816
128/DIG. 20
5,617,027 A * 4/1997 Decke .................. G01R 33/341
324/318

(Continued)

FOREIGN PATENT DOCUMENTS

CN 1785119 A 6/2006
CN 201387480 Y 1/2010

(Continued)

OTHER PUBLICATIONS

First Office Action in Chinese Application No. 201710758535.9 dated Mar. 2, 2020, 32 pages.

*Primary Examiner* — Jason M Ip
(74) *Attorney, Agent, or Firm* — Metis IP LLC

(57) ABSTRACT

The disclosure relates to a system for immobilizing and supporting a subject in a medical procedure. The system may include a treatment apparatus configured to generate a radiation beam, and a device for immobilizing a subject. The device may include an immobilizing component for immobilizing at least one portion of the subject, and a radio frequency (RF) coil configured to receive a magnetic resonance (MR) signal related to the at least one portion of the subject. The immobilizing component may be configured to switch between a first mode and a second mode. The first mode may correspond to a positive pressure or a constant pressure related to the device. The second mode may correspond to a space of vacuum or substantially of vacuum related to the device. The RF coil may be located in the immobilizing component according to a position where the radiation beam is incident on the device.

16 Claims, 7 Drawing Sheets

(56) References Cited

U.S. PATENT DOCUMENTS

| | | | | |
|---|---|---|---|---|
| 5,945,827 | A | * | 8/1999 | Gronauer ......... G01R 33/34046 |
| | | | | 324/318 |
| 6,684,096 | B2 | * | 1/2004 | Schmit ................ A61B 6/0442 |
| | | | | 128/845 |
| 6,818,676 | B2 | | 11/2004 | Koffler et al. |
| 8,984,688 | B1 | * | 3/2015 | Ibrahim ................... A47G 9/10 |
| | | | | 5/632 |
| 9,297,906 | B2 | | 3/2016 | Uhlemann |
| 2002/0079898 | A1 | | 6/2002 | Van De Spijker |
| 2005/0197602 | A1 | | 9/2005 | Kwen |
| 2007/0191706 | A1 | | 8/2007 | Calderon et al. |
| 2007/0285093 | A1 | | 12/2007 | Driemel |
| 2008/0097192 | A1 | | 4/2008 | Driemel |
| 2008/0204021 | A1 | | 8/2008 | Leussler et al. |
| 2009/0012389 | A1 | | 1/2009 | Kundner et al. |
| 2009/0030305 | A1 | * | 1/2009 | Hoogeveen ......... G01R 33/3621 |
| | | | | 600/422 |
| 2013/0218001 | A1 | | 8/2013 | Ni |
| 2013/0310719 | A1 | * | 11/2013 | Davis .................. A61H 9/0085 |
| | | | | 601/149 |
| 2016/0363642 | A1 | | 12/2016 | Gall et al. |
| 2017/0095365 | A1 | * | 4/2017 | Reese ................. A61F 5/05833 |
| 2017/0248666 | A1 | | 8/2017 | Rothgang et al. |

FOREIGN PATENT DOCUMENTS

| | | |
|---|---|---|
| CN | 102028470 A | 4/2011 |
| CN | 202179539 U | 4/2012 |
| CN | 202342699 U | 7/2012 |
| CN | 104689487 A | 6/2015 |
| CN | 204709661 U | 10/2015 |
| CN | 204767061 U | 11/2015 |
| CN | 205163926 U | 4/2016 |

* cited by examiner

DEVICE FOR IMMOBILIZING A SUBJECT IN A MEDICAL SYSTEM

CROSS-REFERENCE OF RELATED APPLICATIONS

This application claims priority of Chinese Patent Application No. 201710758535.9, filed on Aug. 29, 2017, the contents of which are hereby incorporated by reference.

TECHNICAL FIELD

The present disclosure generally relates to a medical system, and more particularly, relates to a magnetic resonance imaging (MRI) system and/or a radiation treatment system.

BACKGROUND

Magnetic resonance imaging (MRI) has been widely used in medical diagnosis, radiation therapy planning, surgery planning and other medical procedures. The MRI technology makes use of one or more gradient pulses to encode spatial information to MR signals for reconstructing images. The MR signals may be collected by one or more radio frequency (RF) coils (e.g., local coils). In some embodiments, the RF coils (e.g., the local coils) may be located far from a patient, which may attenuate the MR signals collected by the RF coils. The attenuation of the MR signals may incur noises and/or artifacts in the images reconstructed based on the received MR signals. Thus, it may be desirable to provide systems and methods for decreasing the attenuation of MR signals collected by the RF coils.

SUMMARY

In a first aspect of the present disclosure, a device for immobilizing and supporting a subject in a medical procedure is provided. The device may include an immobilizing component for immobilizing at least one portion of the subject, and a radio frequency (RF) coil configured to transmit and/or receive a magnetic resonance (MR) signal. The shape of the immobilizing component may be changeable to conform to the portion of the subject. The RF coil may be coupled to the immobilizing component.

In some embodiments, the RF coil may be located in the immobilizing component.

In some embodiments, the RF coil may be detachably coupled to the immobilizing component.

In some embodiments, the device may further comprise a first chamber defined by a first surface and a second chamber defined by a second surface and the first surface, and the radio frequency coil may be detachably coupled to the first surface.

In some embodiments, the first chamber or the second chamber may be at least partially filled with at least one filler material.

In some embodiments, the filler material may comprise at least one filler material of foam particles, sponge, or cotton.

In some embodiments, the first surface and the second surface may be selectively connected with each other via a first connector.

In some embodiments, the first surface may comprise a second connector configured to close an opening on the first surface.

In some embodiments, the second surface may comprise a valve configured to control a gas pressure in the immobilizing component of the device.

In some embodiments, the device may be configured to operate in at least one of a first mode and a second mode. The first mode may correspond to a positive pressure or a constant pressure related to the immobilizing component of the device. The second mode may correspond to a space of vacuum or substantially of vacuum related to the immobilizing component of the device.

In some embodiments, the device may be further configured to switch between the first mode and the second mode.

In some embodiments, a shape of the device in the second mode may be defined according to a shape of the at least one portion of the subject.

In some embodiments, the device may further comprise a communication port connected to the RF coil through which a signal collected by the RF coil may be transmitted to an external device.

In some embodiments, the RF coil may comprise at least one local coil.

In some embodiments, the RF coil may be arranged according to a shape of the at least one portion of the subject.

In some embodiments, the magnetic resonance (MR) signal may relate to the at least one portion of the subject.

In some embodiments, the device may further comprise a chamber housing the RF coil and the immobilizing component.

In a second aspect of the present disclosure, a system for immobilizing and supporting a subject in a medical procedure is provided. The system may include a treatment apparatus configured to generate a radiation beam, and a device for immobilizing a subject. The device may include an immobilizing component for immobilizing at least one portion of the subject, and a radio frequency (RF) coil configured to receive a magnetic resonance (MR) signal related to the at least one portion of the subject. The immobilizing component may be configured to switch between a first mode and a second mode. The first mode may correspond to a positive pressure or a constant pressure related to the device. The second mode may correspond to a space of vacuum or substantially of vacuum related to the device. The RF coil may be coupled to the immobilizing component.

In some embodiments, the RF coil may be located in the immobilizing component according to a position where the radiation beam is incident on the device.

In a third aspect of the present disclosure, a vacuum cushion for immobilizing a subject is provided. The vacuum cushion may include a shell, a filler material contained within a region defined by the shell, and a radio frequency (RF) coil. The radio frequency (RF) coil may be detachably coupled to the vacuum cushion and configured to receive a magnetic resonance (MR) signal related to at least one portion of the subject. The vacuum cushion may have a first mode in which the filler material moves within the region defined by the shell, and a second mode conformed to the contour of the at least one portion of the subject.

In a fourth aspect of the present disclosure, a heat formable cushion for immobilizing a subject is provided. The heat formable cushion may include a shell, a filler material contained within a region defined by the shell, and a radio frequency (RF) coil. The radio frequency (RF) coil may be detachably coupled to the heat formable cushion and configured to receive a magnetic resonance (MR) signal related to at least one portion of the subject. The heat formable cushion may have a first mode in which the filler material moves within the region defined by the shell, and a second mode conformed to the contour of the at least one portion of the subject.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

The following description is presented to enable any person skilled in the art to make and use the present disclosure, and is provided in the context of a particular application and its requirements. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but is to be accorded the widest scope consistent with the claims.

The terminology used herein is for the purpose of describing particular exemplary embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including", when used in this specification, specify the presence of stated features, integers, steps, operations, elements, and/or components, but do not preclude the presence or addition of one or more other features, integers, steps, operations, elements, components, and/or groups thereof.

It will be understood that the term "system," "engine," "unit," and/or "module" used herein are one method to distinguish different components, elements, parts, section or assembly of different level in ascending order. However, the terms may be displaced by another expression if they achieve the same purpose.

Figure 1A:
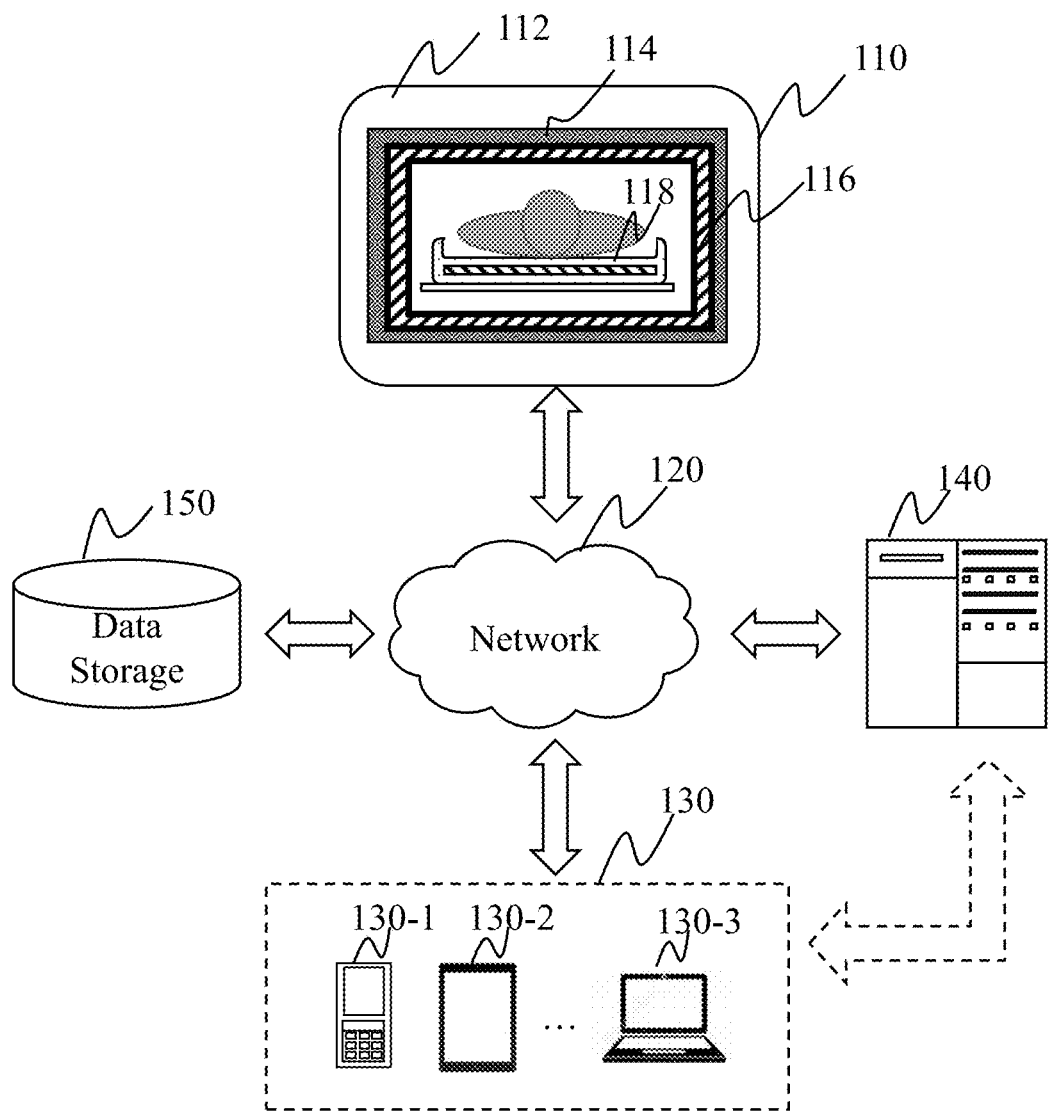
FIGS. 1A and 1B are schematic diagrams illustrating an exemplary MRI system according to some embodiments of the present disclosure.
Figure 1B:
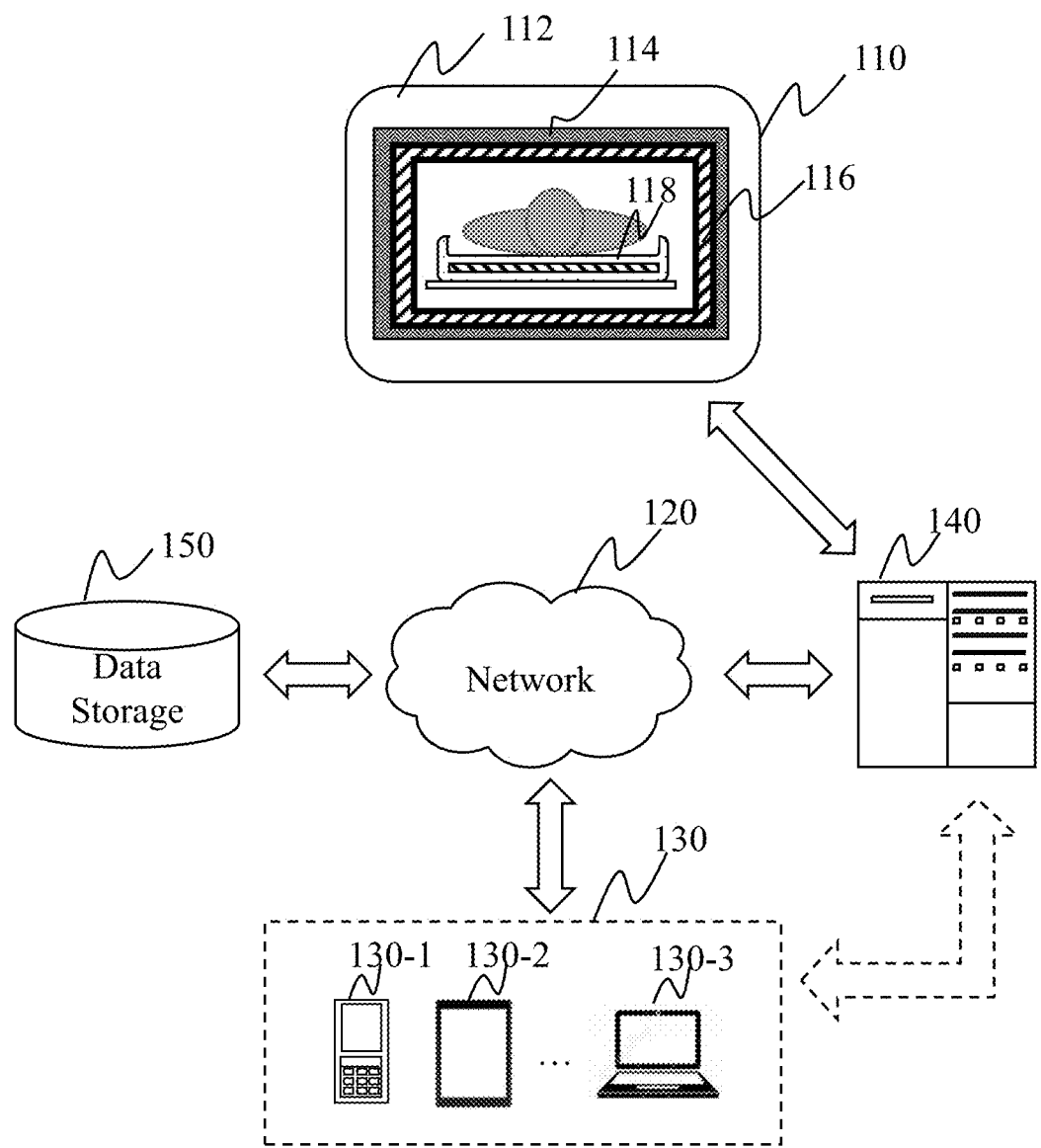

Generally, the word "module" or "unit" as used herein, refers to logic embodied in hardware or firmware, or to a collection of software instructions. A module or a unit described herein may be implemented as software and/or hardware and may be stored in any type of non-transitory computer-readable medium or another storage device. In some embodiments, a software module/unit may be compiled and linked into an executable program. It will be appreciated that software modules can be callable from other modules/units or themselves, and/or may be invoked in response to detected events or interrupts. Software modules/units configured for execution on computing devices (e.g., processing engine 140 as illustrated in FIG. 1A and FIG. 1B) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in firmware, such as an EPROM. It will be further appreciated that hardware modules/units may be included in connected logic components, such as gates and flip-flops, and/or can be included of programmable units, such as programmable gate arrays or processors. The modules/units or computing device functionality described herein may be implemented as software modules/units but may be represented in hardware or firmware. In general, the modules/units described herein refer to logical modules/units that may be combined with other modules/units or divided into sub-modules/sub-units despite their physical organization or storage. The description may apply to a system, an engine, or a portion thereof.

It will be understood that when a unit, engine or module is referred to as being "on," "connected to," or "coupled to," another unit, engine, or module, it may be directly on, connected or coupled to, or communicate with the other unit, engine, or module, or an intervening unit, engine, or module may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of the present disclosure. It is to be expressly understood, however, that the drawings are for the purpose of illustration and description only and are not intended to limit the scope of the present disclosure. It is understood that the drawings are not to scale.

Provided herein are systems and components for medical imaging and/or medical treatment. In some embodiments, the medical system may include an imaging system. The imaging system may include a single modality imaging system and/or a multi-modality imaging system. The single modality imaging system may include, for example, a magnetic resonance imaging (MRI) system. Exemplary magnetic resonance imaging (MRI) system may include a superconducting magnetic resonance imaging device, a non-superconducting magnetic resonance imaging system, etc. The multi-modality imaging system may include, for example, a computed tomography-magnetic resonance imaging (MRI-CT) system, a positron emission tomography-magnetic resonance imaging (PET-MRI) system, a single photon emission computed tomography-magnetic resonance imaging (SPECT-MRI) system, a digital subtraction angiography-magnetic resonance imaging (DSA-MRI) system, etc. In some embodiments, the medical system may include a treatment system. The treatment system may include a treatment plan system (TPS), an image-guide radiotherapy (IGRT), etc. The image-guide radiotherapy (IGRT) may include a treatment device and an imaging device. The treatment device may include a linear accelerator, a cyclotron, a synchrotron, etc., being configured to perform a radio therapy on a subject. The treatment device may include an accelerator of species of particles including, for example, photons, electrons, protons, or heavy ions. The imaging device may include an MRI scanner, a CT scanner (e.g., cone beam computed tomography (CBCT) scanner), a digital radiology (DR) scanner, an electronic portal imaging device (EPID), etc.

For illustration purposes, the disclosure describes systems and methods for MRI medical applications (e.g., MRI imaging, MRI guided radiotherapy treatment, etc.). It should be noted that the MRI system 100 described below is merely provided for illustration purposes, and not intended to limit the scope of the present disclosure.

FIGS. 1A and 1B are schematic diagrams illustrating an exemplary MRI system 100 according to some embodiments of the present disclosure. As shown in FIGS. 1A and 1B, the MRI system 100 may include an MR scanner 110, a network 120, a terminal 130, a processing engine 140, and a data storage 150. The connection between the components in the MRI system 100 may be variable. Merely by way of example, as illustrated in FIG. 1A, the MR scanner 110 may be connected to the processing engine 140 through the network 120. As another example, as illustrated in FIG. 1B, the MR scanner 110 may be connected to the processing engine 140 directly.

The MR scanner 110 may scan at least one portion of the subject.

The subject may be biological or non-biological. Merely by way of example, the subject may include a patient, a man-made object, etc. As another example, the subject may include a specific portion, organ, and/or tissue of the patient. For example, the subject may include head, brain, neck, body, shoulder, arm, thorax, cardiac, stomach, blood vessel, soft tissue, knee, feet, or the like, or any combination thereof. In some embodiments, the MR scanner 110 may receive an MR signal related to the at least portion of the subject. In some embodiments, the MR scanner 110 may generate an MR image based on the received MR signal.

As illustrated in FIGS. 1A and 1B, the MR scanner 110 may include a magnetic body 112, a gradient coil 114, a body coil 116, and an immobilizing device 118. In some embodiments, the location of the immobilizing device 118 in the MR scanner 110 may be adjustable. For example, the location of the immobilizing device 118 may be adjusted by a user (e.g., a patient, a doctor, a nurse, etc.). In some embodiments, the location of the immobilizing device 118 may be adjusted according to the location of a radiation beam (e.g., X-rays, electron rays, photon rays, etc.) in a treatment procedure. The radiation beam may be generated by a treatment apparatus (not shown). As used herein, the treatment apparatus may refer to an apparatus configured to apply a radiation therapy to a subject placed in the MRI system 100. In some embodiments, the treatment apparatus may be located inside or out of the MRI system 100.

The magnetic body 112 may generate a static magnetic field during the scanning of the at least one portion of the subject. The magnetic body 112 may be of various types including, for example, a permanent magnet, a superconducting electromagnet, a resistive electromagnet, etc.

The gradient coil 114 may provide magnetic field gradients to the main magnetic field in an X direction, a Y direction, and/or a Z direction. As used herein, the X direction, the Y direction, and the Z direction may represent an X axis, a Y axis, and a Z axis in a coordinate system. Merely by way of example, the X axis and the Z axis may be in a horizontal plane, the X axis and the Y axis may be in a vertical plane, the Z axis may be along the axis of the magnetic body 112. In some embodiments, the gradient coil(s) 114 may include an X-direction coil for providing a magnetic field gradient to the main magnetic field in the X direction, a Y-direction coil for providing a magnetic field gradient to the main magnetic field in the Y direction, and/or Z-direction coil for providing a magnetic field gradient to the main magnetic field in the Z direction. In some embodiments, the X-direction coil, the Y-direction coil, and/or the Z-direction coil may be of various shape or configuration. For example, the Z-direction coil may be designed based on circular (Maxwell) coil. As another example, the X-direction coil and the Y-direction coil may be designed on the basis of the saddle (Golay) coil configuration.

The body coil 116 may emit signals to and/or receive MR signals from at least one portion of a subject being scanned. As illustrated in connection with the MR scanner 110, the subject may include a patient, at least a portion, a tissue, or an organ of the patient. In some embodiments, the body coil 116 may be an RF coil. The RF coil may be configured to emit RF signals to the subject being examined. In some embodiments, the body coil 116 may include a transmitting coil and a receiving coil. The transmitting coil may emit signals (e.g., RF signals) that may excite a nucleus in the subject to provide a resonation. The receiving coil may receive MR signals emitted from the subject. In some embodiments, the RF transmitting coil and RF receiving coil may be integrated into the same coil. In some embodiments, the body coil 116 may be of various types including, for example, a QD orthogonal coil, a phase-array coil, etc.

The immobilizing device 118 may be configured to immobilize the at least portion of the subject being scanned and receive an MR signal related to the at least portion of the subject. Merely by way of example, the immobilizing device 118 may include, for example, a vacuum cushion containing an RF coil, a heat formable cushion containing an RF coil, etc. As another example, the immobilizing device 118 may include a vacuum cushion and an RF coil located outside the vacuum cushion, a heat formable cushion and an RF coil located outside the heat formable cushion, etc. The RF coil may be detachably coupled to the immobilizing component (e.g., the vacuum cushion, the heat formable cushion) by bonding, for example, through an adhesive tape, a zipper, etc. The immobilizing device 118 may include an immobilizing component and/or a coil. In some embodiments, the immobilizing device 118 may include an immobilizing component for immobilizing the at least a portion of the subject. The immobilizing component may include, for example, a vacuum cushion or a heat formable cushion for supporting the at least a portion of the subject. As used herein, a vacuum cushion may refer to a cushion the pressure inside which may be changed to be vacuum or to be less than the ambient atmospheric pressure. A heat formable cushion may refer to a cushion that may be deformed by the application of heat.

An exemplary vacuum cushion may include a shell, and a filler material (e.g., a plurality of filler particles) contained in the shell. The void in the vacuum cushion may be occupied by a filling material including, e.g., air. For illustration purposes, the description below is provided with reference to air as the filling material. In some embodiments, the vacuum cushion may include a plurality of cells air-permeably separated from each other such that there may be air exchange between cells. A cell may contain one or more filler particles, the movement of which are restricted in the cell.

The vacuum cushion may have a working configuration and a non-working configuration. The vacuum cushion may be considered to be in its working configuration when it has the shape conforming to a subject or a portion thereof to be examined and the shell encloses a space of vacuum or substantially of vacuum. As used herein, a space of vacuum may indicate that the space is void of the air. As used herein, a space substantially of vacuum may indicate that the pressure within the space is at least 60%, or 70%, or 80%, or 90% lower than the ambient atmospheric pressure. The vacuum cushion may maintain the working configuration until the vacuum or substantial vacuum of the space enclosed in the shell is destroyed. The vacuum cushion may be considered to be in a non-working configuration when it is not in its working configuration. When the vacuum cushion is in a non-working configuration, its shape does not conform to a subject or a portion thereof to be examined, and/or the shell encloses a space of positive pressure or constant pressure. As used herein, the positive pressure may refer to a pressure larger than the ambient atmospheric pressure, and the constant pressure may refer to a pressure that is close to or equal to the ambient atmospheric pressure. For instance, the pressure within the space is at least 60%, or 70%, or 80%, or 90% of the ambient atmospheric pressure.

An exemplary heat formable cushion may include a shell that is applied with a thermoplastic material. Another exemplary heat formable cushion may include a shell, and a filler material contained within a region defined by the shell. The filler material of the heat formable cushion may include a thermoplastic material. The heat formable cushion may be deformed by the application of heat.

In some embodiments, the immobilizing device 118 may include a coil (not shown). The coil may include an RF coil. The coil (e.g., the RF coil) may receive an MR signal related to the at least a portion of the subject and/or emit a signal (e.g., an RF signal) thereto. In some embodiments, the RF coil may include a local coil. As used herein, a local coil may refer to a coil configured to emit RF pulses to and/or receive MR signals related to a local region of the subject being scanned. Merely by way of example, the local coil may be a surface coil including, for example, a head coil, knee coil, an ankle joint coil, a cervical vertebra coil, a thoracic vertebra coil, a temporomandibular joint (TMJ) coil, a breast coil, an endorectal coil, an abdomen array coil, a head-neck phase-array coil, a body phase-array coil, a double leg array coil, a total spine phase-array coil, etc. As another example, the coil may include a birdcage coil, a solenoid coil, a saddle coil, a Helmholtz coil, a phased array coil, a transverse electromagnetic coil, a loop coil, or the like, or a combination thereof.

In some embodiments, the immobilizing device 118 may include a vacuum cushion having a first mode (or referred to a non-working configuration) and/or a second mode (or referred to a working configuration). The immobilizing device 118 may be considered to be in its working configuration when it has the shape conforming to a subject or a portion thereof to be examined and includes a space of vacuum or substantially of vacuum for housing a filler material (e.g., cells containing filler particles) such that the immobilizing device 118 may maintain the shape until the vacuum or substantial vacuum of the space is destroyed. The immobilizing device 118 may be considered to be in a non-working configuration when it is not in its working configuration. When the immobilizing device 118 is in a non-working configuration, its shape does not conform to a subject or a portion thereof to be examined, and/or the pressure within the space for housing the filler material is close to, equal to, or higher than the ambient atmospheric pressure. The meanings of the terms vacuum, substantial vacuum, a pressure close to the ambient atmospheric pressure used herein are similar to those used in the description of a vacuum cushion, and not repeated here.

In some embodiments, the second mode of the immobilizing device 118 (e.g., a vacuum cushion) may be configured to conform to the contour of at least a portion of the subject placed on it. For example, the vacuum cushion may include a plurality of air-permeable cells that are configured to contain a plurality of filler particles. The movement of one or more filler particles within a cell may be restricted within the cell. The cells may be air-permeably separated from each other. When the at least a portion of the subject is placed on the vacuum cushion, the vacuum cushion may be deformed according to the contour of the at least a portion of the subject. At least a portion of the air in the vacuum cushion may be removed (e.g., through a valve on the vacuum cushion) by, for example, a load relating to the at least portion of the subject supported by the vacuum cushion, the suction force generated by a vacuum pump, or the like, or a combination thereof. The load relating to the subject or a portion thereof may be due to the weight of the subject or a portion thereof (e.g., when the subject or a portion thereof is placed on or otherwise supported by the vacuum cushion), or a force to compress the vacuum cushion against the subject or a portion thereof (e.g., when the vacuum cushion is wrapped around or otherwise secured on the subject or a portion thereof). The removal of air from the vacuum cushion may result in the second mode of the vacuum cushion from the first mode. The volume of at least a portion of the air-preamble cells may be decreased, and the filler particles contained in the at least one air-permeable cell may be further restrained from movement as compared to that when the vacuum cushion is in the first mode, and packed according to the contour of or the load relating to the subject or a portion thereof. Then, the vacuum cushion in the second mode may conform to the contour of the at least portion of the subject placed on it.

In some embodiments, the immobilizing device 118 may include a heat formable cushion having a first condition and/or a second condition corresponding to different configurations of the immobilizing device 118. In some embodiments, the second condition of the immobilizing device 118 (e.g., a heat formable cushion) may be configured to conform to the contour of at least portion of the subject supported on the immobilizing device 118 or on which the immobilizing device 118 is secured. For example, the heat formable cushion may include a thermoplastic material that may deform by heat. When at least portion of subject is placed on the heat formable cushion that is in a first condition, a heat source may be used to deform the thermoplastic material such that the heat formable cushion change to a second condition. The second condition of the heat formable cushion may conform to the contour of at least portion of the subject supported on the heat formable cushion or on which the heat formable cushion is secured. When cooled down to, e.g., the room temperature, the thermoplastic material may become rigid, and the heat formable cushion may become a rigid cushion maintaining its shape conforming to the contour of the at least portion of the subject.

In some embodiments, the MR scanner 110 may be a permanent magnet MR scanner, a superconducting electromagnet MR scanner, or a resistive electromagnet MR scanner, etc. In some embodiments, the MR scanner 110 may be a high-field MR scanner, a mid-field MR scanner, and a low-field MR scanner, etc.

In some embodiments, the MR scanner 110 may be connected to or communicate with the terminal 130, the processing engine 140 and/or the storage device. In some embodiments, the MR scanner 110 may transmit the MR signal and/or image data to the terminal(s) 130, the processing engine 140, and/or the storage device 150, via the network 120. For example, the MR scanner 110 may send the MR signal and/or the image data to the processing engine 140 for further processing.

The network 120 may include any suitable network that can facilitate the exchange of information and/or data for the MRI system 100. In some embodiments, one or more components of the MRI system 100 (e.g., the MR scanner 110, the terminal(s) 130, the processing engine 140, the data storage 150, etc.) may communicate information and/or data with one or more other components of the MRI system 100 via the network 120. For example, the processing engine 140 may obtain MR signals from the MR scanner 110 via the network 120. As another example, the processing engine 140 may obtain user instructions from the terminal(s) 130 via the network 120. The network 120 may be and/or include a public network (e.g., the Internet), a private network (e.g., a local area network (LAN), a wide area network (WAN)), etc.), a wired network (e.g., an Ethernet network), a wireless network (e.g., an 502.11 network, a Wi-Fi network, etc.), a cellular network (e.g., a Long Term Evolution (LTE) network), a frame relay network, a virtual private network ("VPN"), a satellite network, a telephone network, routers, hubs, witches, server computers, and/or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the MRI system 100 may be connected to the network 120 to exchange data and/or information.

The terminal(s) 130 may include a mobile device 130-1, a tablet computer 130-2, a laptop computer 130-3, or the like, or any combination thereof. In some embodiments, the mobile device 130-1 may include a smart home device, a wearable device, a mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, footgear, eyeglasses, a helmet, a watch, clothing, a backpack, a smart accessory, or the like, or any combination thereof. In some embodiments, the mobile device may include a mobile phone, a personal digital assistance (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal(s) 130 may be part of the processing engine 140.

Figure 2:
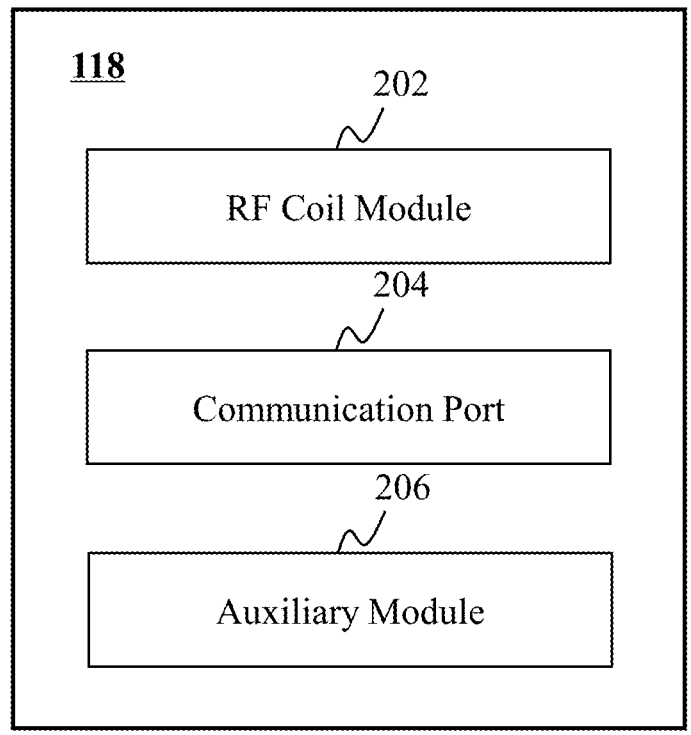
FIG. 2 is a block diagram illustrating an exemplary immobilizing device according to some embodiments of the present disclosure.

The processing engine 140 may process data and/or information obtained from the MR scanner 110, the terminal(s) 130, and/or the data storage 150. For example, the processing engine 140 may process MR signals generated by the scanner 110 and encode the MR signals for reconstructing an image. As another example, the processing engine 140 may determine a lesion (e.g., a tumor) in the reconstructed image and determine a treatment plan associated with the lesion based on the reconstructed image. In some embodiments, the processing engine 140 may be a single server or a server group. The server group may be centralized or distributed. In some embodiments, the processing engine 140 may be local or remote. For example, the processing engine 140 may access information and/or data stored in the MR scanner 110, the terminal(s) 130, and/or the data storage 150 via the network 120. As another example, the processing engine 140 may be directly connected to the MR scanner 110, the terminal(s) 130 and/or the data storage 150 to access stored information and/or data. In some embodiments, the processing engine 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing engine 140 may be implemented by a computing device 200 having one or more components as illustrated in FIG. 2.

The data storage 150 may store data, instructions, and/or any other information. In some embodiments, the data storage 150 may store data obtained from the terminal(s) 130 and/or the processing engine 140. In some embodiments, the data storage 150 may store data and/or instructions that the processing engine 140 may execute or use to perform exemplary methods described in the present disclosure. In some embodiments, the data storage 150 may include a mass storage, removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the data storage 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the data storage 150 may be connected to the network 120 to communicate with one or more other components in the MRI system 100 (e.g., the processing engine 140, the terminal(s) 130, etc.). One or more components of the MRI system 100 may access the data or instructions stored in the data storage 150 via the network 120. In some embodiments, the data storage 150 may be directly connected to or communicate with one or more other components in the MRI system 100 (e.g., the processing engine 140, the terminal(s) 130, etc.). In some embodiments, the data storage 150 may be part of the processing engine 140.

This description is intended to be illustrative, and not to limit the scope of the present disclosure. Many alternatives, modifications, and variations will be apparent to those skilled in the art. The features, structures, methods, and characteristics of the exemplary embodiments described herein may be combined in various ways to obtain additional and/or alternative exemplary embodiments. However, those variations and modifications do not depart the scope of the present disclosure. For example, the body coil 116 may be omitted. The function of the body coil 116 (e.g., receiving MR signals and/or emitting RF pulses) may be performed by the local coil in the immobilizing device 118. As another example, in some embodiments, the MRI system 100 may include a plurality of immobilizing devices 118. The plurality of immobilizing devices 118 may correspond to different parts of a subject (e.g., a patient) being examined. For example, the MRI system 100 may include a first immobilizing device, a second immobilizing device, etc. Merely by way of example, the first immobilizing device may be configured to immobilize an arm of the patient being examined and collect MR signals therefrom, while the second immobilizing device may be configured to immobilize a leg of the patient being examined and collect MR signals therefrom. In some embodiments, the plurality of the immobilizing devices 118 (e.g., the first immobilizing device and the second immobilizing device) may operate synchronously in an imaging procedure and/or in a treatment procedure.

FIG. 2 is a block diagram illustrating an exemplary immobilizing device 118 according to some embodiments of the present disclosure. As shown in FIG. 2, the immobilizing device 118 may include a radio frequency (RF) coil module 202, a communication port 204, and an auxiliary module 206.

The RF coil module 202 may emit RF signals to and/or receive MR signals from a part of the subject being examined. As described in connection with the immobilizing device 118, the subject may include a patient, or an organ, a tissue of the subject, or a part thereof. The RF coil module 202 may include a certain number of RF coils. An RF coil may include a local coil (e.g., a surface coil). In some embodiments, the number of the RF coils included in the RF coil module 202 may be changed. Merely by way of example, at least one of the RF coils included in the RF coil module 202 may be taken out of the immobilizing device 118. As another example, at least one extra RF coil may be put into the RF coil module 202 of the immobilizing device 118. In some embodiments, an RF coil may be taken out of or put into the RF coil module 202 through an opening as illustrated below in the present disclosure. In some embodiments, the number of the RF coils included in the RF coil module 202 may relate to the shape and/or size of the part of the subject being examined. Merely by way of example, one RF coil may be included in the RF module 202 when the subject being examined is a finger of a patient. As another example, 3 to 5 RF coils may be included in the RF module 202 when the subject being examined is a palm of the patient. The RF coils included in the RF coil module 202 may be arranged depending on one or more factors including, for example, the size or shape of the part of the subject being examined. For example, the RF coils may be arranged in a circle when the part of the subject being examined (e.g., a head) is approximately cylindrical or spherical in shape. In some embodiments, at least one coil of the RF coils included in the RF coil module 202 may be located at a position spaced apart from a position where a radiation beam is incident on the immobilizing device 118, to prevent the RF coils from being located in the pathway of the radiation beam (e.g., X-rays, electron rays, photon rays, etc.). The radiation beam may be generated by a treatment apparatus illustrated elsewhere in the present disclosure. The distance between the RF coil and the position where the radiation beam is incident on the immobilizing device 118 may be at least, for example, 1 centimeter, 2 centimeters, 3 centimeters, 5 centimeters, etc.

The communication port 204 may provide a connection between the RF coil module 202 and an external device not included by the immobilizing device 118. In some embodiments, the external device may include a device included in one or more components of the MRI system 100 (e.g., the terminal 130, the processing engine 140, the data storage 150). Merely by way of example, the external device may include a smart home device, a wearable device, a mobile device, a virtual reality device, an augmented reality device, or the like, or any combination thereof.

The communication port 204 may provide a connection between the RF coil module 202 and one or more components of the MRI system 100. In some embodiments, the RF coil module 202 may transmit the MR signals to the one or more components of the MRI system 100 through the communication port 204. Merely by way of example, the communication port 204 may provide a connection between the RF coil module 202 and the processing engine 140, and transmit an MR signal collected by the RF coil module 202 to the processing engine 140 for further processing. In some embodiments, the connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee link, a mobile network link (e.g., 3G, 4G, 5G, etc.), or the like, or a combination thereof. In some embodiments, the communication port 204 may be and/or include a standardized communication port, such as RS232, RS485, etc. In some embodiments, the communication port 204 may be a specially designed communication port. For example, the communication port 204 may be designed in accordance with the digital imaging and communications in medicine (DICOM) protocol.

The auxiliary module 206 may be configured to support and/or immobilize at least portion of the subject being scanned. The auxiliary module 206 may be in various forms, such as a cushion, a bag, or the like, or a combination thereof.

In some embodiments, the auxiliary module 206 may be configured to house the RF coil module 202. Merely by way of example, the RF coil module 202 may locate inside of the auxiliary module 206 (e.g., a cushion). In some embodiments, the auxiliary module 206 may include at least one chamber housing the RF coil module 202. For example, the auxiliary module 206 may include a chamber. The RF coil module 202 may be located in the chamber. As another example, the auxiliary module 206 may include a first chamber and a second chamber different from the first chamber. For instance, the first chamber and the second chamber may be configured side by side, one on top of the other, etc. In some embodiments, the first chamber and the second chamber may be spaced apart. The RF coil module 202 may be placed inside of the first chamber, while the second chamber is at least partially filled with a filler material. In some embodiments, the first chamber may be at least partially filled with a filler material, in addition to the RF coil module 202. In some embodiments, the first chamber may house the RF coil module 202 without a filler material. In some embodiments, the filler material in the first chamber and/or the second chamber may be at least one filler material including, e.g., foam particles, sponge, cotton, or the like, or a combination thereof. In some embodiments, the auxiliary module 206 may include a first surface forming the first chamber. The first chamber may house the RF coil module 202. As another example, the auxiliary module 206 may further include a second surface enclosing the first surface. The second chamber may be formed between the first surface and the second surface. In some embodiments, at least one portion of the second surface and at least one portion of the first surface may be connected by a first connector, such as a zipper. In some embodiments, the first surface and/or the second surface may include an opening. The opening may be configured to take the RF coils out of the auxiliary module 206. In some embodiments, the opening may be closed by a second connector, for example, a zipper.

In some embodiments, the first chamber and/or the second chamber may include at least one filler material. The filler material may include foam particles, sponge, cotton, or the like, or a combination thereof. The foam particles may include one or more polymer materials such as resin, fiber, rubber, etc. The resin may include phenolic, urea-formaldehyde, melamine-formaldehyde, epoxy, polyurethane, polyimide, polymethyl methacrylate (PMMA), acrylonitrile butadiene styrene (ABS), polyamide, polylactic acid (PLA), polybenzimidazole (PBI), polycarbonate (PC), polyethersulfone (PES), polyetheretherketone (PEEK), polyethylene (PE), polyphenylene oxide (PPO), polyphenylene sulfide (PPS), polypropylene (PP), polystyrene (PS), polyvinyl chloride (PVC), etc. The sponge may include nature cellulose, foamed resin, etc. The foamed resin may include polyether, polyester, polyvinyl alcohol, etc. In some embodiments, the fill rate for the filler material in the first chamber and/or the second chamber may vary depending on the immobilizing requirements of the immobilized device 118.

In some embodiments, the auxiliary module 206 may include a valve. In some embodiments, the valve may be mounted on the first surface or the second surface. The valve may be configured to provide gas communication between the auxiliary module 206 and a source of negative pressure (e.g., a vacuum pump). For example, the pressure in the first chamber and/or the second chamber may be adjusted by the valve and the source of negative pressure (e.g., a vacuum pump). Further, the source of negative pressure (e.g., a vacuum pump) may render the first chamber and/or the second chamber via the valve to include a space of vacuum or substantially of vacuum.

In some embodiments, the auxiliary module 206 may include a bolster. The bolster may be made of one or more rigid or semi-rigid plastics. The rigid or semi-rigid bolster may be movable to provide additional support for a subject being supported by the immobilizing device 118. For example, the bolster may be moved to support a knee of a patient during an imaging procedure or a treatment procedure. As another example, the bolster may be moved to support the underneath of a neck of a patient when the patient is lying on the immobilizing device 118.

In an imaging procedure, when a patient or one portion of the patient is placed on the auxiliary module 206, auxiliary module 206 may be deformed to a shape that accommodates the patient or the portion of the patient. The portion of the patient may include the head, the neck, the body, a shoulder, an arm, the thorax, a knee, a foot, or the like, or any combination thereof. In some embodiments, the shape that accommodates the patient or a portion of the patient may be configured to maintain for a certain time. For example, for a vacuum cushion in the second mode, the shape of the vacuum cushion may maintain until the pressure in the vacuum cushion changes. The auxiliary module 206 may be connected to the source of the negative pressure (e.g., a vacuum pump) via the valve. The source of the negative pressure (e.g., a vacuum pump) may generate a pressure (e.g., vacuum) in the auxiliary module 206 smaller than a pressure outside of the auxiliary module 206, and the auxiliary module 206 may be molded to the patient's contours. The filler material that is previously free-flowing in the auxiliary 206 may be constrained by compression resulting from the atmospheric pressure on the outside of the auxiliary module 206. The RF coils in the RF coil module 202 may become closer to the patient or the portion of the patient for receiving an MR signal related to the patient by the compression resulting from the atmospheric pressure outside of the auxiliary module 206. When the patient or the portion of the patient separates from the auxiliary module 206, the auxiliary module 206 may be still deformed by the compression resulting from the atmospheric pressure outside of the auxiliary module 206, and the deformation of the auxiliary module 206 may be in accordance with the patient's contours. Then in a treatment and subsequent treatment procedures related to the patient, the patient or the portion of the patient may be placed on and positioned by the deformed auxiliary module 206.

This description is intended to be illustrative, and not to limit the scope of the present disclosure. Many alternatives, modifications, and variations will be apparent to those skilled in the art. The features, structures, methods, and characteristics of the exemplary embodiments described herein may be combined in various ways to obtain additional and/or alternative exemplary embodiments. For example, the communication port 204 and the auxiliary module 206 may be combined into one single module. As another example, the immobilizing device 118 may further include a processor. The processor may be connected to the RF coil module 202 for processing MR signals collected by the RF coil module 202. However, those variations and modifications do not depart the scope of the present disclosure.

Figure 3A:
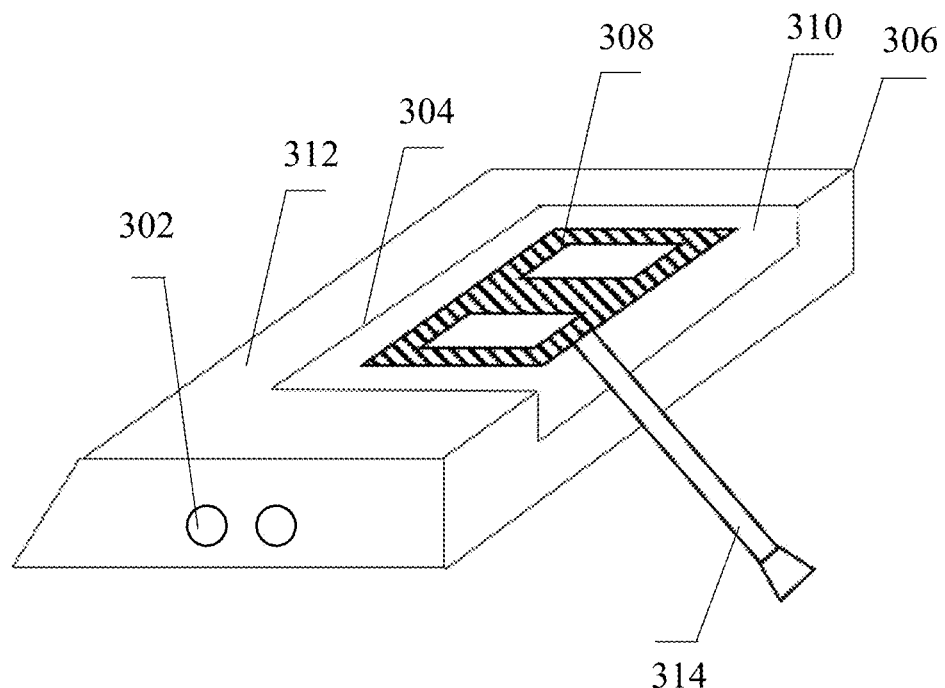
FIG. 3A is a schematic diagram illustrating an exemplary immobilizing device according to some embodiments of the present disclosure.

FIG. 3A is a schematic diagram illustrating an exemplary immobilizing device 300 according to some embodiments of the present disclosure. As shown, the immobilizing device 300 may include a valve 302, a first surface 304, a second surface 306, one or more radio frequency (RF) coils 308, a first chamber 310, a second chamber 312, and a communication port 314.

The first surface 304 may form the first chamber 310. The first chamber 310 may house the radio frequency coils 308. The RF coils 308 may be detachably coupled to the first surface 304 by bonding, for example, through an adhesive tape, a zipper, etc. The RF coils 308 may be detached from the first surface 304 such that the RF coils 308 may be taken out from the immobilizing device 300. Further, in some embodiments, the RF coils 308 taken out from the immobilizing device 300 may be reused. For instance, the RF coils 308 removed from one immobilized device 300 may be placed into another immobilizing device 300. The second surface 306 may enclose the first surface 304. The first surface 304 and/or the second surface 306 may include one or more gas-impermeable materials, such as a nylon cloth or a gas-impermeable coating, such as a polyurethane coating. The second chamber 312 may be formed between the first surface 304 and the second surface 306. The second chamber 312 may enclose the first chamber 310. The second chamber 312 may be filled with at least one filler material as described in connection with FIG. 2.

The valve 302 may be configured on the second surface 306 to provide gas communication between the first chamber 310 and/or the second chamber 312 and a source of negative pressure (e.g., a vacuum pump). The source of negative pressure may be connected to the valve 302 to control a pressure in the first chamber 310 and/or the second chamber 312. For example, when the first surface 304 is gas-impermeable, the valve 302 mounted on the second surface 306 may provide a gas communication between the second chamber 312 and the source of negative pressure (e.g., a vacuum pump). As another example, when the first surface 304 is gas-permeable, the valve 302 mounted on the second surface 306 may provide a gas communication between the first chamber 310, the second chamber 312, and the source of negative pressure (e.g., a vacuum pump).

The communication port 314 may be connected to the RF coils 308 and a network (e.g., the network 120) to establish connections between the RF coils 308 and the processing engine 140, the storage module 408, and/or the data storage 150.

Figure 3B:
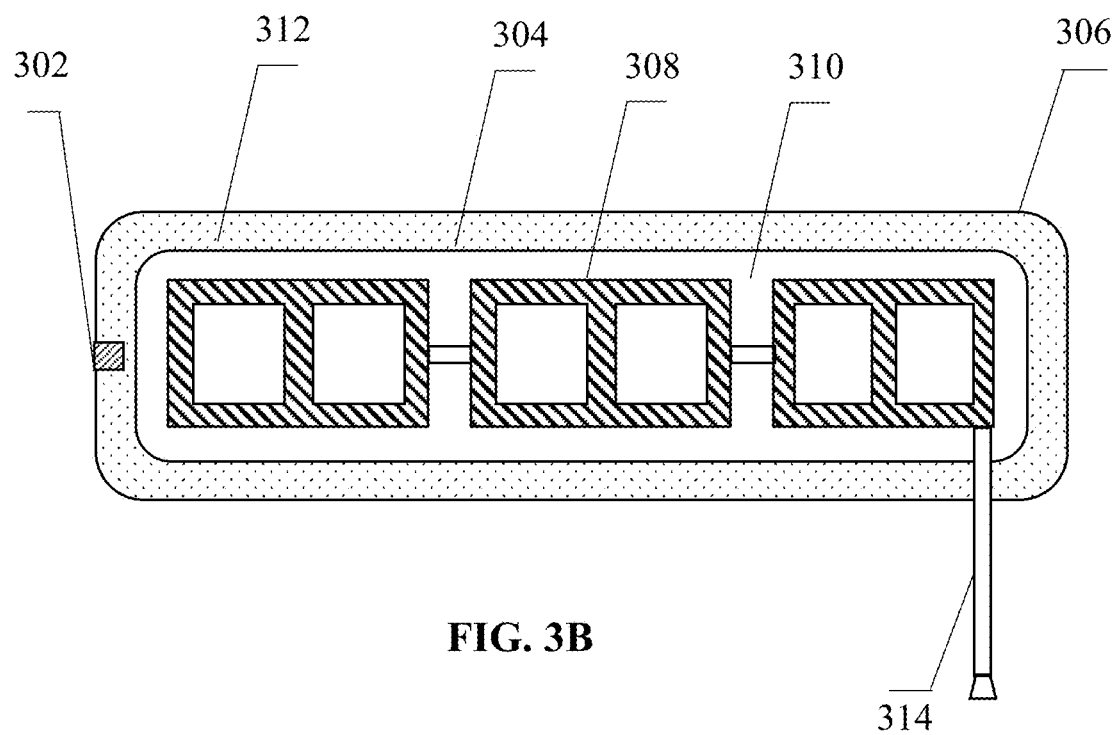
FIG. 3B is a cross-sectional view of an exemplary immobilizing device according to some embodiments of the present disclosure.

FIG. 3B is a cross-sectional view of the exemplary immobilizing device 300 according to some embodiments of the present disclosure. As shown in FIG. 3B, the RF coils 308 may be arranged in the first chamber 310 according to a shape of the immobilizing device 300. The second chamber 312 may be filled with at least one filler material. The filler material may include foam particles, sponge, cotton, or the like, or a combination thereof. The foam particles may include one or more polymer materials such as resin, fiber, rubber, etc. The resin may include phenolic, urea-formaldehyde, melamine-formaldehyde, epoxy, polyurethane, polyimide, polymethyl methacrylate (PMMA), acrylonitrile butadiene styrene (ABS), polyamide, polylactic acid (PLA), polybenzimidazole (PBI), polycarbonate (PC), polyethersulfone (PES), polyetheretherketone (PEEK), polyethylene (PE), polyphenylene oxide (PPO), polyphenylene sulfide (PPS), polypropylene (PP), polystyrene (PS), polyvinyl chloride (PVC), etc. The sponge may include nature cellulose, foamed resin, etc. The foamed resin may include polyether, polyester, polyvinyl alcohol, etc.

Figure 4A:
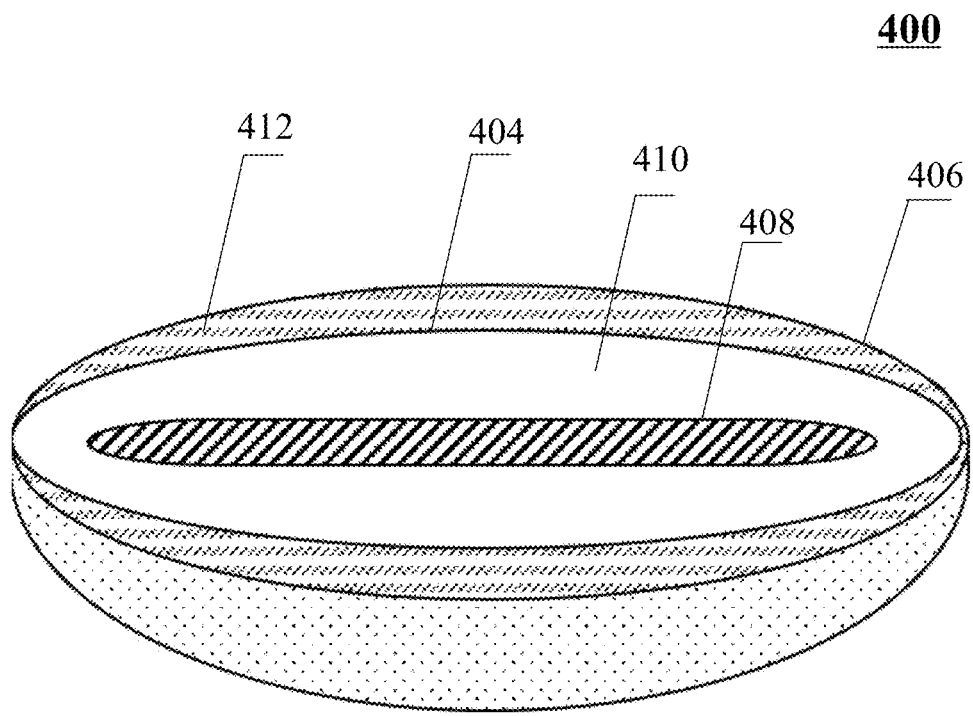
FIG. 4A is a cross-sectional view of the exemplary immobilizing device according to some embodiments of the present disclosure.

FIG. 4A is a cross-sectional view of the exemplary immobilizing device 400 according to some embodiments of the present disclosure. As shown in FIG. 4A, the immobilizing device 400 may include a first surface 404, a second surface 406, a first chamber 410, a second chamber 412, and one or more radio frequency coils 408. In some embodiments, the first chamber 410 may be included in the second chamber 412. In some embodiments, the first chamber 410 and the second chamber 412 may be positioned next to each other or separate from each other. For example, the first chamber 410 may be formed by the first surface 404. The second chamber 412 may be formed by the second surface 406. At least one portion of the first surface 404 and at least one portion of the second surface 406 may be connected to each other through a first connector, for example, a zipper.

Figure 4B:
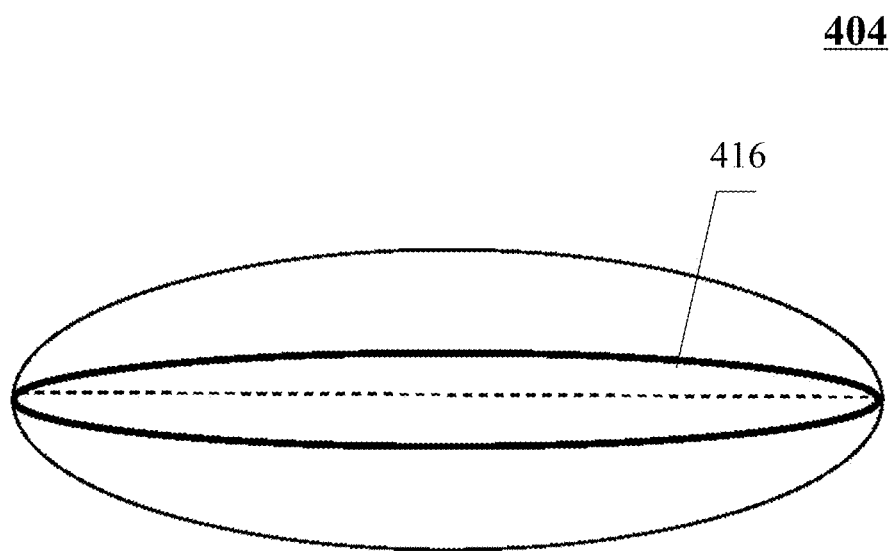
FIG. 4B is a schematic diagram illustrating the first surface according to some embodiments of the present disclosure.

FIG. 4B is a schematic diagram illustrating the first surface according to some embodiments of the present disclosure. The first surface 404 may include an opening (not shown in FIG. 4B) and a second connector 416 configured to close the opening (e.g., a closed opening represented by the dotted line as shown in FIG. 4B). The second connector 416 may include, for example, a zipper. The radio frequency coils 408 may be taken out of the first chamber 410 through the opening.

FIGS. 5A-5D are exemplary cross-sectional view illustrating immobilizing devices according to some embodiments of the present disclosure.

Figure 5A:
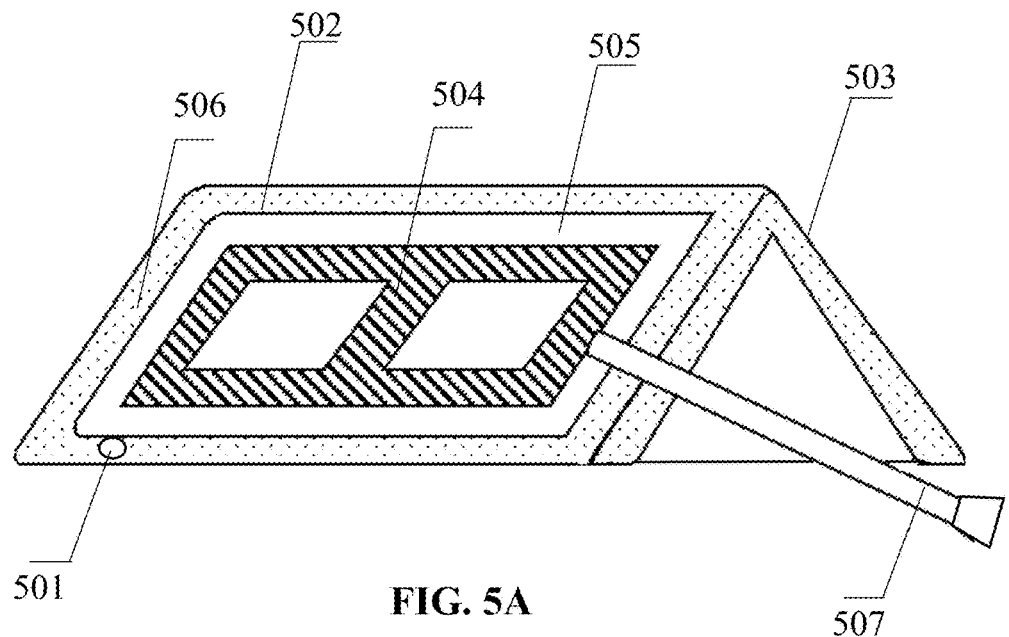
FIGS. 5A-5D are exemplary cross-sectional views illustrating immobilizing devices according to some embodiments of the present disclosure.

As shown in FIG. 5A, an immobilizing device 500 may include a valve 501, a first surface 502, a second surface 503, a radio frequency coil 504, a first chamber 505, a second chamber 506, and a communication port 507. The immobilizing device 500 may have a triangle structure, which may be suitable for a knee. For example, the immobilizing device 500 in the triangle structure may cover and immobilize a knee of the patient.

Figure 5B:
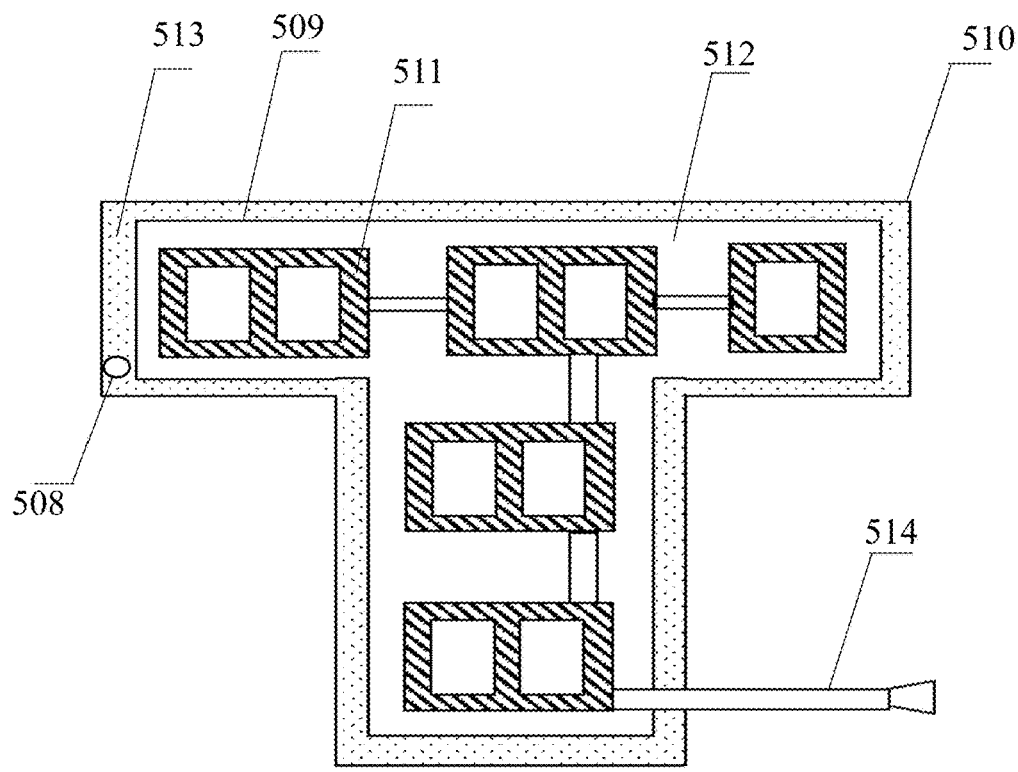

As shown in FIG. 5B, an immobilizing device 530 may include a valve 508, a first surface 509, a second surface 510, a radio frequency coil 511, a first chamber 512, a second chamber 513, and a communication port 514. The immobilizing device 530 may have a T-shape structure configured to immobilize a torso or an arm of a patient in an imaging procedure or a treatment procedure.

Figure 5C:
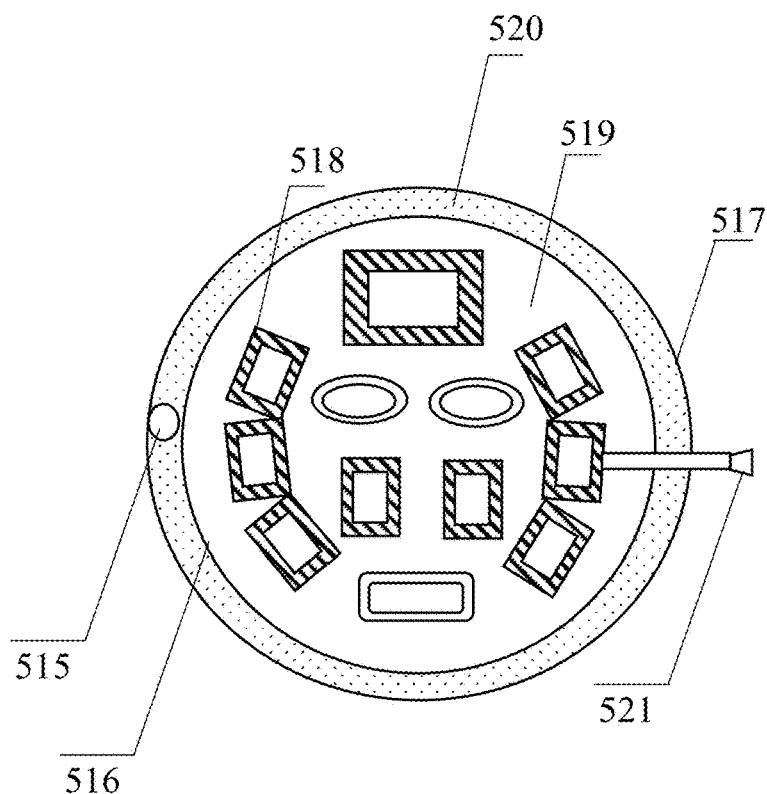

As shown in FIG. 5C, an immobilizing device 560 may include a valve 515, a first surface 516, a second surface 517, a radio frequency coil 518, a first chamber 519, a second chamber 520, and a communication port 521. The immobilizing device 560 may have a circular structure configured to immobilize the face or head of a patient in an imaging procedure or a treatment procedure. The radio frequency coils 518 may be arranged according to the shape of the immobilizing device 560.

Figure 5D:
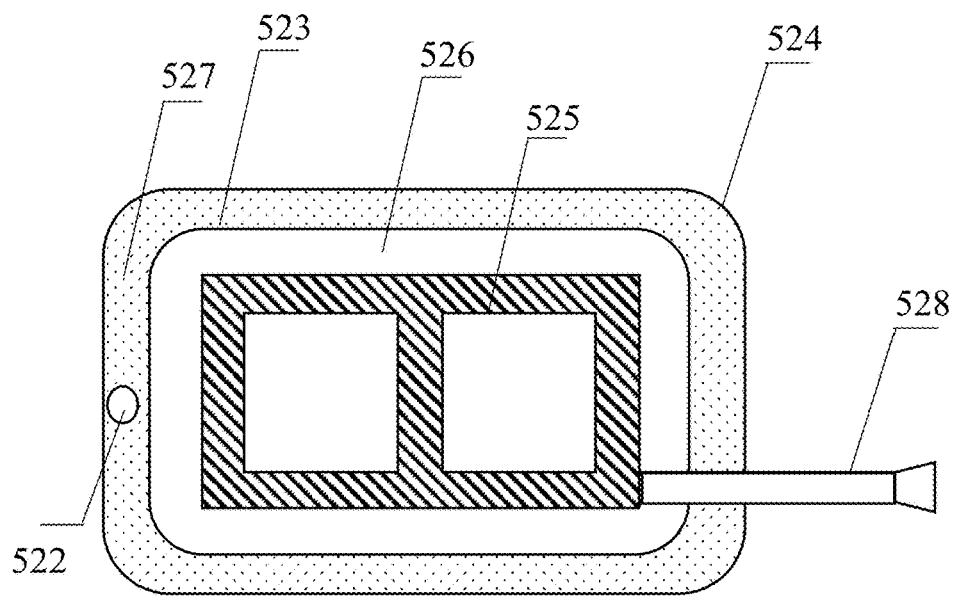

As shown in FIG. 5D, an immobilizing device 590 may include a valve 522, a first surface 523, a second surface 524, a radio frequency coil 525, a first chamber 526, a second chamber 527, and a communication port 528. The immobilizing device 590 may be configured to immobilize a portion of a patient, for example, a hand, a foot, a neck, a breast, a finger, a toe, a joint, etc. The immobilizing device 590 may be of a shape (or size) corresponding to the shape of the portion of the patient.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by the present disclosure, and are within the spirit and scope of the exemplary embodiments of the present disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, radio frequency (RF), or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C #, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations, therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose and that the appended claims are not limited to the disclosed embodiments, but, on the contrary, are intended to surface modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

I claim:

1. A device for immobilizing a subject in a medical procedure, the device comprising:
    a cushion that immobilizes at least one portion of the subject, wherein the shape of the cushion is changeable to conform to the portion of the subject; and
    multiple radio frequency (RF) coils configured to transmit or receive a magnetic resonance (MR) signal, wherein the cushion includes a first chamber defined by a first surface and a second chamber defined by a second surface and the first surface, the multiple RF coils are located in the first chamber,
    the second chamber includes a plurality of air-permeable cells separated from each other, each cell of the plurality of air-permeable cells containing filler particles, movement of the filler particles being restricted within the cell,
    the device is configured to switch between a first mode and a second mode,
    a change of a volume of each of at least a portion of the plurality of air-permeable cells causes a switch between the first mode and the second mode, and
    the movement of the filler particles contained in at least one air-permeable cell is more restrained when the device is in the second mode as compared to when the device is in the first mode.

2. The device of claim 1, wherein the first chamber is at least partially filled with at least one filler material.

3. The device of claim 2, wherein the filler material comprises at least one filler material of foam particles, sponge, or cotton.

4. The device of claim 1, wherein the first surface and the second surface are selectively connected with each other via a first connector, the first connector including a zipper.

5. The device of claim 1, wherein the first surface comprises a second connector that closes an opening on the first surface, the second connector including a zipper.

6. The device of claim 1, wherein the second surface comprises a valve configured to control a gas pressure in the cushion of the device.

7. The device of claim 1, wherein the first mode corresponds to a positive pressure or a constant pressure related to the cushion of the device, and the second mode corresponds to a space of vacuum related to the cushion of the device.

8. The device of claim 7, wherein a shape of the device in the second mode is defined according to a shape of the at least one portion of the subject.

9. The device of claim 1, wherein the device further comprises a communication port connected to the RF coil through which a signal collected by the RF coil is transmitted to an external device.

10. The device of claim 1, wherein the RF coils comprise at least one local coil.

11. The device of claim 1, wherein the MR signal relates to the at least one portion of the subject.

12. The device of claim 1, wherein the device further comprises a chamber housing the multiple RF coils and the cushion.

13. A vacuum cushion for immobilizing a subject, comprising:
    a shell;
    a filler material contained within a region defined by the shell; and
    multiple radio frequency (RF) coils which are detachably coupled to the vacuum cushion and configured to receive a magnetic resonance (MR) signal related to at least one portion of the subject, wherein the vacuum cushion has a first mode in which the filler material moves within the region defined by the shell, and a second mode conformed to the contour of the at least one portion of the subject, wherein the vacuum cushion includes a chamber defined by a surface located in the region, the multiple radio frequency (RF) coils are coupled to the surface and located in the chamber, the chamber includes a plurality of air-permeable cells separated from each other, each cell of the plurality of air-permeable cells containing filler particles, movement of the filler particles being restricted within the cell,
    the vacuum cushion is configured to switch between the first mode and the second mode,
    a change of a volume of each of at least a portion of the plurality of air-permeable cells causes a switch between the first mode and the second mode, and
    the movement of the filler particles contained in at least one air-permeable cell is more restrained when the device is in the second mode as compared to when the vacuum cushion is in the first mode.

14. The device of claim 1, wherein the first surface is detachably connected to the second surface.

15. The device of claim 1, wherein at least one of a distribution or a count of the multiple RF coils arranged in the first chamber is changeable according to at least one of a size, a shape, or a location of the at least a portion of the subject.

16. The device of claim 1, wherein the multiple RF coils are detachably coupled to the first surface.

* * * * *